US010775299B2

(12) United States Patent
Quaderer

(10) Patent No.: US 10,775,299 B2
(45) Date of Patent: Sep. 15, 2020

(54) OPTICAL TUNING FOR PLANT DETECTION

(71) Applicant: Trimble Inc., Sunnyvale, CA (US)

(72) Inventor: James G. Quaderer, Sunnyvale, CA (US)

(73) Assignee: Trimble Inc., Sunnyvale, CA (US)

(*) Notice: Subject to any disclaimer, the term of this patent is extended or adjusted under 35 U.S.C. 154(b) by 39 days.

(21) Appl. No.: 16/282,211

(22) Filed: Feb. 21, 2019

(65) Prior Publication Data
US 2020/0217785 A1    Jul. 9, 2020

Related U.S. Application Data

(60) Provisional application No. 62/789,920, filed on Jan. 8, 2019.

(51) Int. Cl.
G01N 21/27      (2006.01)
G01N 33/00      (2006.01)
G01N 21/35      (2014.01)
A01M 7/00       (2006.01)
A01M 21/04      (2006.01)

(52) U.S. Cl.
CPC ......... *G01N 21/274* (2013.01); *A01M 7/0089* (2013.01); *A01M 21/043* (2013.01); *G01N 21/35* (2013.01); *G01N 33/0098* (2013.01); *G01N 2201/0627* (2013.01); *G01N 2201/12746* (2013.01)

(58) Field of Classification Search
CPC .. G01N 21/274; G01N 21/35; G01N 33/0098; G01N 2201/0627; G01N 2201/12746; A01M 7/0089; A01M 21/043
See application file for complete search history.

(56) References Cited

U.S. PATENT DOCUMENTS

| | | | | |
|---|---|---|---|---|
| 5,296,702 A * | 3/1994 | Beck | ................... | A01M 7/0089 |
| | | | | 250/226 |
| 5,763,873 A * | 6/1998 | Beck | ..................... | G01J 1/4204 |
| | | | | 250/214 B |
| 5,789,741 A | 8/1998 | Kinter et al. | | |
| 6,424,416 B1 * | 7/2002 | Gross | ........................ | G01J 3/02 |
| | | | | 356/326 |
| 6,601,341 B2 | 8/2003 | Raun et al. | | |
| 6,836,325 B2 * | 12/2004 | Maczura | ................... | G01J 3/02 |
| | | | | 356/328 |

(Continued)

OTHER PUBLICATIONS

UltraCMOS® Digitally Tunable Capacitor, pSemi, PE64101, 4 pages, downloaded Feb. 21, 2019 at https://www.psemi.com/products/digitally-tunable-capacitors-dtc/pe64101.

(Continued)

*Primary Examiner* — Dominic J Bologna
(74) *Attorney, Agent, or Firm* — Kilpatrick Townsend & Stockton LLP

(57) ABSTRACT

A Light Emitting Diode (LED) is added to a weed control system for calibrating the weed control system. A detector generates an electrical signal based on receiving light emitted by the LED. An electronically-tunable capacitor of a bandpass filter is adjusted based the signal received from the detector to adjust a center frequency of the bandpass filter so that light from an optical source, different from the LED, can more efficiently be detected by the weed control system.

20 Claims, 6 Drawing Sheets

(56) References Cited

U.S. PATENT DOCUMENTS

| | | | | |
|---|---|---|---|---|
| 8,189,189 | B1* | 5/2012 | Herendeen | G01J 3/501 |
| | | | | 356/300 |
| 10,178,828 | B2 | 1/2019 | Hendrickson et al. | |
| 2003/0155487 | A1* | 8/2003 | Reime | G01S 3/783 |
| | | | | 250/221 |
| 2005/0098713 | A1* | 5/2005 | Holland | G01J 3/10 |
| | | | | 250/221 |
| 2014/0323844 | A1* | 10/2014 | Deliwala | H01L 31/02016 |
| | | | | 600/407 |
| 2015/0075066 | A1* | 3/2015 | Stowe | G06K 9/6267 |
| | | | | 47/1.3 |
| 2016/0025777 | A1* | 1/2016 | Deliwala | A61B 5/02427 |
| | | | | 324/115 |
| 2016/0377530 | A1* | 12/2016 | Barrett | G01J 3/108 |
| | | | | 250/564 |
| 2017/0339839 | A1* | 11/2017 | Carstensen | H05B 45/10 |

OTHER PUBLICATIONS

Digi-Key Electronics, DuNE™ Enhanced Digitally Tunable Capacitor, 2 pages, downloaded Feb. 21, 2019 at https://www.digikey.com/en/product-highlight/p/peregrine-semi/dune-enhanced-digitally-tunable-capacitor.

Frenzel, L. "Digitally Tunable Capacitor Lets You Build Variable Filters, Z-Matches, and More," Jul. 26, 2011, 3 pages downloaded Feb. 21, 2019 at https://www.electronicdesign.com/communications/digitally-tunable-capacitor-lets-you-build-variable-filters-z-matches-and-more.

* cited by examiner

OPTICAL TUNING FOR PLANT DETECTION

CROSS REFERENCES TO RELATED APPLICATIONS

This application claims priority to U.S. Provisional Application No. 62/789,920, filed on Jan. 8, 2019, the disclosure of which is incorporated by reference in its entirety for all purposes.

FIELD OF THE INVENTION

Embodiments described herein relate generally to plant detection systems, and more particularly, to controlling plant detection systems.

BACKGROUND

The spectral reflectance of a plant compared to that of soil can be used to detect the presence of a plant on the ground. This is shown in FIG. 1, which is an exemplary plot illustrating the reflectance versus wavelength of a living plant 1 compared to that of bare soil 2. Due to the differences between the spectral reflectance characteristics, it is possible to differentiate the living plant 1 from the bare soil 2. For example, light beams of two different wavelengths $W_1$, $W_2$ can be transmitted toward the ground, and the intensities of the different wavelengths of scattered light returning from the ground are compared to determine if there is a plant 1 or just bare soil 2.

Detecting a plant in this manner can be useful to reduce the amount of herbicide required to eradicate weeds in a field. For example, a field may be scanned using light beams of two different wavelengths, and each time the spectral reflectance characteristic of a weed is detected, a valve may be opened to spray herbicide on the weed. A considerable savings in herbicide may be realized since it is not sprayed unnecessarily onto the bare soil. See U.S. Pat. No. 5,789,741, granted on Aug. 4, 1998, for an example of a device used for detecting plants in the field.

Improved methods and/or systems for detecting the presence of plants on the ground are desired.

SUMMARY

Embodiments described herein generally provide, without limitation, improved systems and/or methods for optically tuning a system to detect plants.

In some embodiments, a system for distributing herbicide comprises: a housing; an optical detector in the housing; a first optical source, wherein the first optical source is configured to be driven at a first frequency and/or the first optical source is oriented in the housing so that light from the first optical source does not have a straight optical path to exit the housing; an electrical network electrically coupled with the optical detector, the electrical network comprising a bandpass filter configured to pass an electrical signal, wherein the bandpass filter is centered at a second frequency; and/or a controller configured to electronically adjust an electrical component of the bandpass filter to align the second frequency with the first frequency, such that the electrical network is calibrated for passing a modulated signal generated by the optical detector sensing light emitted from a second optical source modulated at the first frequency. In some embodiments, the system further comprises the second optical source; the second optical source is oriented in the housing so that light from the second optical source has a straight optical path to exit the housing; the system further comprises a third optical source; the third optical source is oriented in the housing so that light from the third optical source has a straight optical path to exit the housing; the third optical source has a different optical spectrum than the first optical source and the second optical source; the first optical source emits green light, the second optical source emits red light, and the third optical source emits light in the infrared; the second optical source is configured to direct light to the ground; the optical detector is configured to detect light reflected from the ground or an object on the ground; the controller is configured to activate a switch to spray herbicide in response to the optical detector detecting light reflected from a plant; the second frequency aligning with the first frequency is the second frequency equal to the first frequency, plus or minus 5%; light from the first optical source does not have an optical path to exit the housing; there is not a straight optical path from the first optical source to the optical detector; light from the first optical source is configured to reflect from the housing before reaching the optical detector; the first optical source is configured to run at less than half maximum power; the bandpass filter comprises a capacitor, and the capacitor is a digital capacitor; the bandpass filter comprises an inductor; and/or the electrical network further comprises a transimpedence amplifier and a zero-cross detector.

In some embodiments, a method for calibrating and using an herbicide system comprises: emitting light from a first optical source, wherein: the first optical source is modulated at a first frequency, and/or the first optical source is oriented in a housing so that light from the first optical source does not have a straight optical path to exit the housing; detecting light emitted from the first optical source using an optical detector; adjusting a bandpass filter, which is part of an electrical network electrically coupled with the optical detector, using a controller wherein: the bandpass filter is centered at a second frequency, and/or the bandpass filter is adjusted based on feedback from light detected by the optical detector from light emitted by the first optical source, so that the second frequency is aligned with the first frequency; emitting light from a second optical source, wherein: the second optical source is mounted in the housing, and/or the second optical source has a straight optical path from the second optical source to the ground; and/or determining that light emitted from the second optical source is at least partially absorbed by an object on the ground based on electrical signals from the optical detector and the second frequency being aligned with the first frequency. In some embodiments, the object on the ground is a plant; the method further comprises activating a sprayer to spray a chemical on the plant based on the optical detector detecting that light from the second optical source is at least partially absorbed by the object.

In some embodiments, a system distributing herbicide comprises: a housing; an optical detector in the housing; a first optical source, wherein: the first optical source is configured to be driven at a first frequency, and/or the first optical source is oriented in the housing to reflect light from the housing to be detected by the optical detector; an electrical network electrically coupled with the optical detector, the electrical network comprising a bandpass filter configured to pass an electrical signal, wherein the bandpass filter is centered at a second frequency; and/or a controller configured to electronically adjust an electrical component of the bandpass filter to align the second frequency with the first frequency, such that the electrical network is calibrated for passing a modulated signal generated by the optical detector sensing light emitted from a second optical source modulated at the first frequency. In some embodiments, the first optical source is configured in the housing to emit light to reflect off a panel of the housing to be detected by the optical detector after reflecting off the panel; the panel is transparent or semitransparent; and/or the panel in the housing is configured to not pass light from the first optical source toward the ground while the system is in use.

DETAILED DESCRIPTION

Embodiments described herein provide, without limitation, improved plant detection systems and methods. In some plant detection systems, a bandpass filter is used to detect light emitted by a pulsed light source. A controller is used to modulate a light source at a modulation frequency. A detector (e.g., a photodiode) is used to detect pulses of light and generate an electrical signal, wherein the electrical signal will have a frequency of the modulation frequency based on the pulses of light. The bandpass filter is used to filter electrical signals from the photodiode. If the bandpass filter is centered on the modulation frequency, a signal from the light source is allowed to pass, and electrical signals from noise (e.g., ambient light, such as sunlight reflected by a plant) will be blocked. Thus it can be beneficial for the bandpass filter to be centered on the modulation frequency because the system will have a better signal-to-noise ratio.

The bandpass filter can be calibrated at the factory by installing an electrical jumper that passes a modulation signal to the bandpass filter. However, a jumper can become a parasitic element during operation of the system (e.g., adding parasitic inductance). Additionally, several factors (e.g., temperature, vibrations, humidity) can cause a center frequency of the bandpass filter to drift, making it more difficult for the system to detect light emitted from the light source. One way to calibrate the system in the field is to have a user change a set screw of an inductor of the bandpass filter to change the center frequency of the bandpass filter to align with the modulation frequency. This can take time away from operation and relies on user performance.

Instead of having a user adjust a set screw, the bandpass filter can be calibrated electrically to be centered on the modulation frequency. An LED is added for calibrating the detector. The LED is placed in a housing with the detector so that light from the LED is received by the detector. The LED is modulated at the modulation frequency. The bandpass filter is adjusted based on a signal from the detector corresponding to light emitted by the LED. An electronically-adjustable capacitor of the bandpass filter is adjusted to maximize the electrical signal during calibration. After calibration, the optical source is modulated at the modulation frequency and used to detect plants. By electrically adjusting the bandpass filter, the system can be calibrated on the fly and/or with little input by the user (e.g., the user can simply press a button and the system will calibrate). In some embodiments, the system calibrates at startup and/or periodically during use.

Figure 1:
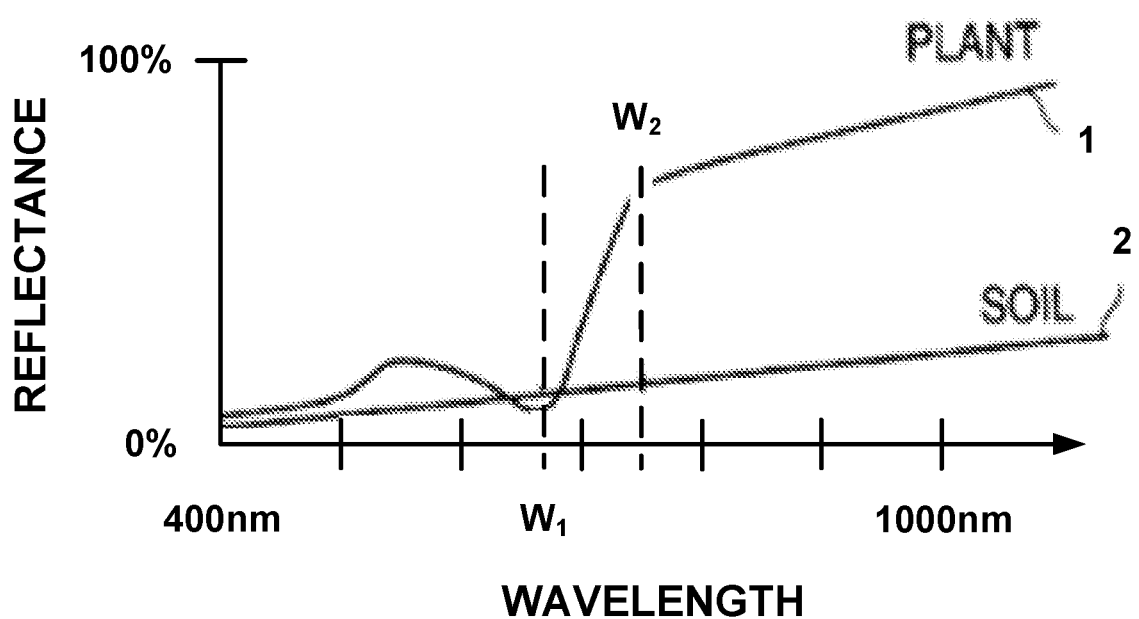
FIG. 1 is a plot illustrating the spectral reflectance of a living plant compared to that of soil.
Figure 2:
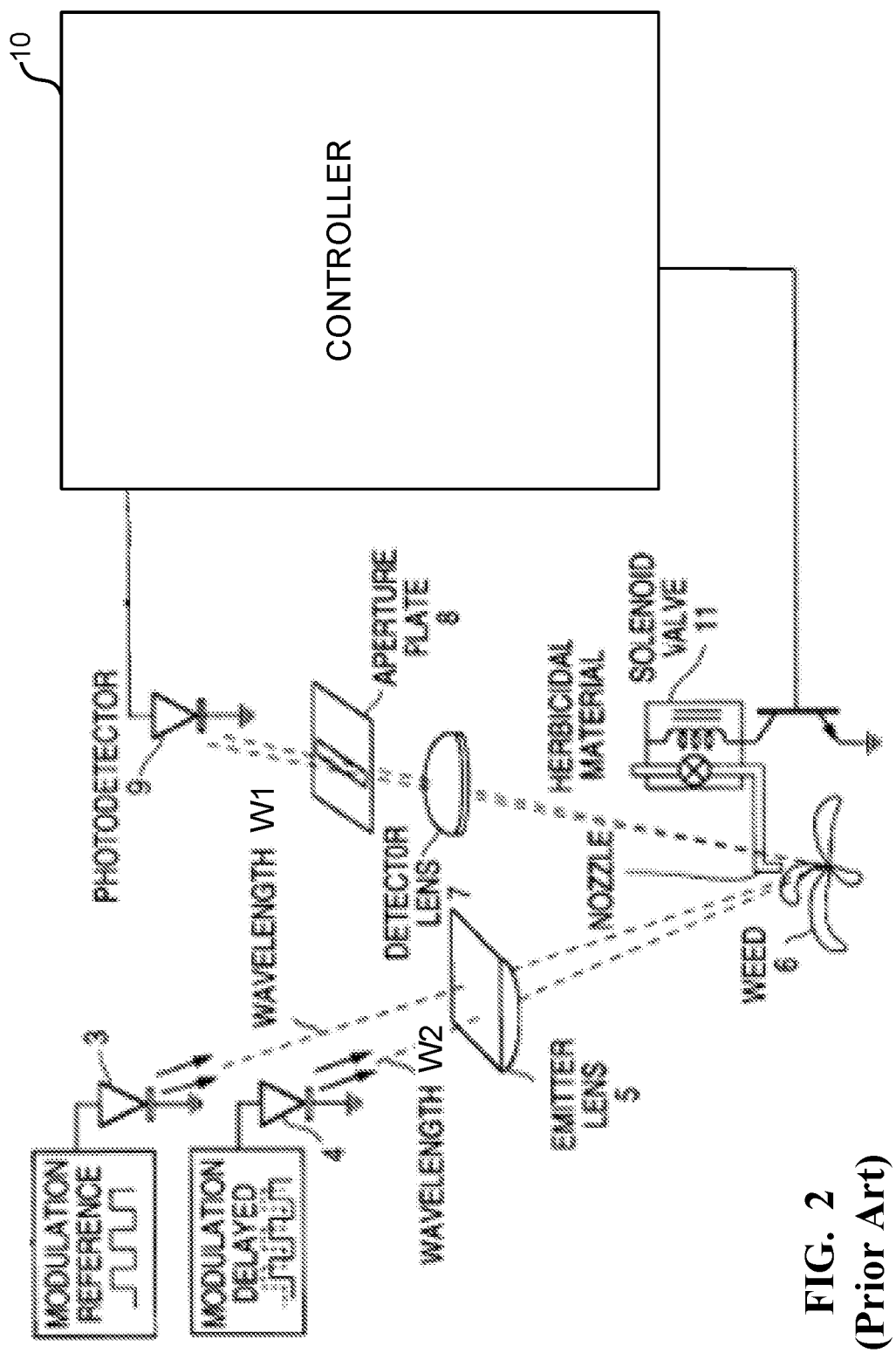
FIG. 2 is a simplified schematic diagram of an exemplary herbicide sprayer system.

FIG. 2 is a simplified schematic diagram of an exemplary herbicide sprayer system that may benefit from the embodiments described herein. The herbicide sprayer system is used merely as an example, and it should be appreciated that the embodiments described herein may be used with other types of plant-detection systems.

In the herbicide sprayer system shown in FIG. 2, a first diode 3 emits light at a first wavelength (wavelength W1) and a second diode 4 emits light at a second wavelength (wavelength W2). In this example, drive currents of the diodes 3, 4 are each modulated with respective modulation signals that are of the same frequency but different phase. The light from the diodes 3, 4 passes through an emitter lens 5 and is directed toward an object on the ground (in this case a plant, weed 6). Some of the light impinging on the weed 6 is reflected and passes through a detector lens 7 and an aperture plate 8 before impinging on a photodetector 9.

Light impinging upon the photodetector 9 is used to assess the spectral reflectance characteristic of the scattered light and therefore to characterize the object (e.g., the weed 6 on the ground) from which the light is scattered. For example, if the light from the diode 4 were completely absorbed by the weed 6, then the only light received by the photodetector 9 would be from the first diode 3. If, on the other hand, no light from the first diode 3 were scattered from the weed 6, then the only light received by the photodetector 9 would be from the diode 4.

The foregoing example represent extreme cases. In practice, the photodetector 9 typically receives some light from both the first diode 3 and the second diode 4. By analyzing relative reflectance values, a weed 6 can be detected. If detected light is consistent with the spectral reflectance characteristic of a weed 6, then controller 10 provides a signal to open a solenoid valve 11 to spray herbicide onto the weed 6. Conversely, if reflectance information is consistent with a spectral reflectance characteristic of soil, the controller 10 does not provide a signal to the solenoid valve 11, and the solenoid valve 11 remains closed.

It should be appreciated that the schematic diagram shown in FIG. 2 depicts an exemplary herbicide sprayer system. The embodiments described herein are not limited to this system, and they may be implemented in other systems that may include different and/or additional components.

Figure 3:
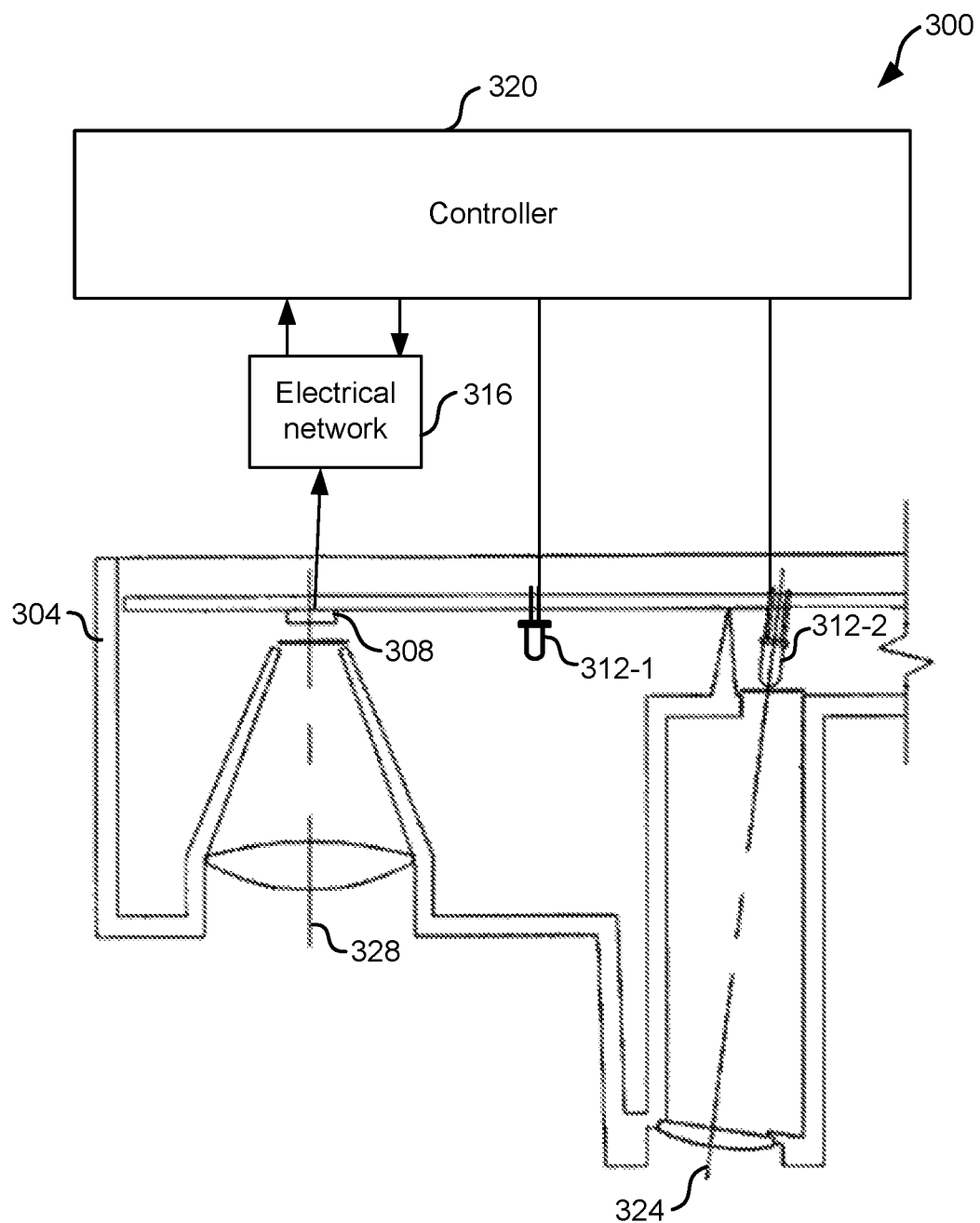
FIG. 3 is a simplified cross-sectional view of a portion of an exemplary herbicide sprayer system.

FIG. 3 is a simplified cross-sectional view of a portion of an exemplary herbicide sprayer system 300. The system 300 comprises a housing 304, an optical detector 308, a first optical source 312-1, a second optical source 312-2, an electrical network 316, and a controller 320.

The first optical source 312-1 and/or the second optical source 312-2 can comprise a light emitting diode (LED). The first optical source 312-1 is configured to be driven at a first frequency. For example, the controller 320 modulates the first optical source 312-1 by sending an electrical signal (e.g., a drive signal) to the first optical source 312-1 so that the first optical source turns off and on according to the first frequency (e.g., the first frequency is 80 kHz, so that the first optical source 312-1 flashes, turns off and on, 80,000 times in one second). The first optical source 312-1 is oriented in the housing 304 so that light from the first optical source 312-1 does not have a straight optical path to exit the housing 304 but can be detected by the optical detector 308 (e.g., by reflection).

The optical detector 308 is configured to generate an electrical signal (e.g., a detect signal) based on an optical signal (e.g., a photodiode converts an optical signal to an electrical signal). The optical detector 308 is oriented in the housing 304 so as to be able to detect light emitted from the first optical source 312-1. For example, light from the first optical source 312-1 reflects off the housing 304 and is detected by the optical detector 308. The optical detector 308 is electrically coupled with the electrical network 316. The electrical network 316 comprises a bandpass filter configured to pass an electrical signal (e.g., to pass the detect signal from the optical detector 308). The bandpass filter is centered at a second frequency, and the bandpass filter has a pass bandwidth (e.g., measured at full-width, half-max).

The controller 320 is configured to electronically adjust an electrical component of the bandpass filter of the electrical network 316 to align the second frequency with the first frequency, such that the electrical network 316 is calibrated for passing a modulated signal (e.g., the detected signal), which is generated by the optical detector 308 sensing light emitted from the second optical source 312-2. For example, the second optical source 312-2 is modulated at the same frequency as the first optical source 312-1.

By having the first optical source 312-1, the system 300 can be calibrated on the fly. For example, the electrical network 316 can be calibrated at a factory. While the system 300 is operating in a field, the first optical source 312-1 can be turned on (e.g., at the same time with the second optical source 312-2 or while the second optical source 312-2 is turned off), and the electrical network 316 recalibrated electrically without a user having to adjust the electrical network 316. In some embodiments, calibrating the electrical network 316 tunes the second frequency to be equal to the first frequency, plus or minus 2, 5, 10, 15 or 20% of the first frequency.

The first optical source 312-1 can have an LED of a different color than the second optical source 312-2. For example, the second optical source 312-2 has two LEDs; though in some embodiments, the second optical source 312-2 has only one LED (e.g., no more than one LED for illuminating a plant; the second optical source could be configured to emit light that stimulates fluorescence in a plant, and the detector could be configured to detect emitted fluorescence light from the plant). The two LEDs emit light at wavelength W1 and wavelength W2. Wavelength W2 is centered on an infrared wavelength, and wavelength W1 is centered on a red wavelength. The first optical source 312-1 could be an LED with an emission spectrum centered on a green wavelength or a blue wavelength (or a red or infrared wavelength). In some embodiments a green LED is used so that a user can see the first optical source 312-1 during calibration (though the first optical source 312-1 doesn't have a direct light path, e.g., a straight line, to exit the housing 304, a user could still see light from the first optical source 312-1 after reflecting within the housing 304 (e.g., light exiting the housing 304 by passing through the detector lens 7).

The second optical source 312-2 is oriented in the housing 304 so that light from the second optical source 312-2 can exit the housing 304 along an optical path 324, wherein the optical path 324 is a straight optical path. Light from the second optical source 312-2 is directed toward the ground to shine on a plant. The optical detector 308 is configured in the housing 304 to detect light reflected from the ground. In some embodiments, the second LED of the second optical source 312-2 is referred to as a third optical source. The third optical source emits light along the optical path 324 or parallel to the optical path 324. Light from the second optical source 312-2 is reflected by the ground and travels along an optical path 328 to the optical detector 308. In FIG. 3, the optical path 324 from the second optical source 312-2 is shown angled and the optical path 328 to the optical detector 308 is shown perpendicular (e.g., a vertical line) with respect to the ground. In other embodiments, the optical path 328 to the optical detector 308 is angled and the optical path 324 from the second optical source 312-2 is perpendicular to the ground (and in some embodiments, both the optical path 324 and the optical path 328 are angled and neither is vertical).

There is not a straight optical path from the first optical source 312-1 to the optical detector 308. The optical detector 308 is configured to detect light from the second optical source 312-2 after light is reflected from the ground. Accordingly, the optical detector 308 is configured to be sensitive to detecting light. Light from the first optical source 312-1 can be too bright for the optical detector 308, so the first optical source 312-1 can be positioned in the housing so that light from the first optical source 312-1 is reflected by the housing 304 before reaching the optical detector 308, and/or the first optical source 312-1 is driven at less than full power (e.g., equal to or less than 50, 30, 20% and/or equal to or greater than 0.5, 1, or 3% of full power). In some embodiments, there is a straight optical path from the first optical source 312-1 to the detector 308 and/or an optical filter is used to attenuate light from the optical source 312-1 before reaching the detector 308.

In some embodiments, the first optical source 312-1 has a direct optical path out of the housing 304, yet the direct optical path out of the housing 304 is not directed toward the ground while the system 300 is configured for use. For example, the first optical source 312-1 could be configured to shine light out a panel (e.g., a transparent or semi-transparent panel made of glass or plastic); such as for a user to see that the system 300 is calibrating the electrical network 316. The first optical source 312-1 and the optical detector 308 can be configured so that the optical detector 308 detects light from the first optical source 312-1 reflected by the panel. The panel is not along the optical path 324 of the second optical source 312-2 or along the optical path 328 of the optical detector 308. For example, the panel can be a button pressed by the user that runs a calibration process to align the second frequency with the first frequency. While the calibration process is running, light from the first optical source 312-1 is used to illuminate the button and also used to calibrate the electrical network 316, which can reduce a number of light sources used in the system 300. In some embodiments, the panel is part of the housing 304. In some embodiments, light from the first optical source 312-1 has a direct optical path to exit the housing, while some of the light reaches the optical detector 308 (e.g., by reflection).

In actual implementations, a plurality of the herbicide sprayer systems may be arranged adjacent to each other on an implement that is coupled to a tractor or another type of farm equipment. A height of the herbicide sprayer systems above the ground may be adjusted to provide nearly full coverage of the ground under the implement. Light emitted from the herbicide sprayer systems generally have little to no overlap on the ground to avoid detection and double spraying of plants by adjacent systems.

Figure 4:
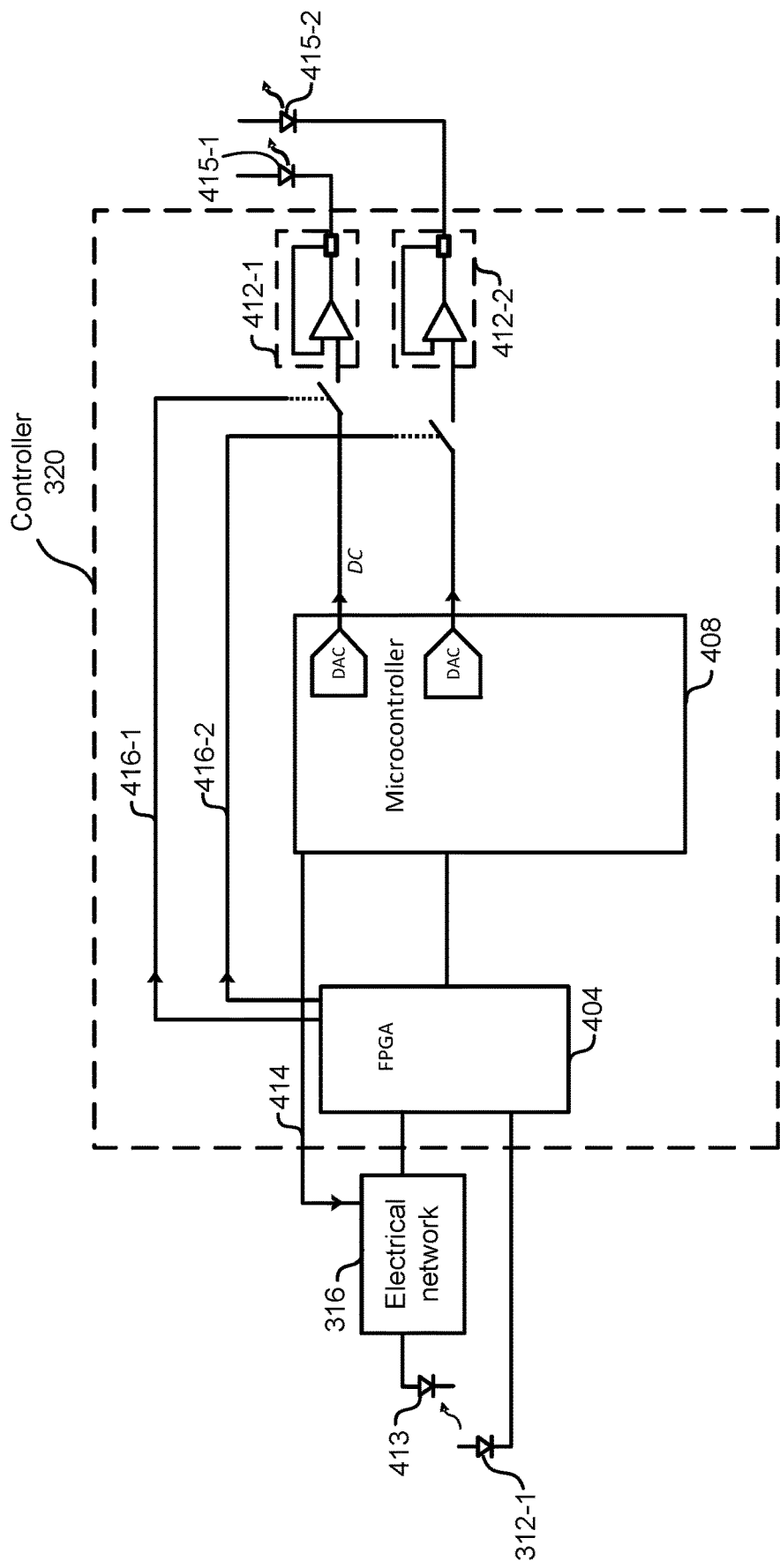
FIG. 4 is a simplified diagram of an embodiment of a control system for an herbicide sprayer system.

FIG. 4 depicts a simplified diagram of an embodiment of a controller 320 for an herbicide sprayer system. The controller 320 comprises a Field Programmable Gate Array (FPGA) 404, a microcontroller 408, and LED drivers 412. The FPGA 404 sends a drive signal to the first optical source 312-1. The drive signal is modulated at the first frequency. The first optical source 312-1 emits flashes of light at the first frequency, based on the drive signal (e.g., the first optical source 312-1 flashes at 80 kHz). A receive photodiode 413, which is part of the optical detector 308, generates a detect signal, which is passed to the electrical network 316. A bandpass filter of the electrical network 316 passes the detect signal to the microcontroller 408 (e.g., via the FPGA 404). The bandpass filter is centered on a second frequency. The microcontroller adjusts (e.g., electrically using a tuning connection 414) one or more component of the bandpass filter so that the second frequency aligns with the first frequency (e.g., adjusts to a local power maximum of the detect signal; aligning can be adjusting the second frequency so that the second frequency equals the first frequency, plus or minus 1, 5, 10, 15%; and/or adjusting the second frequency so that the second frequency equals the first frequency, plus or minus 5, 10, or 20 kHz).

The FPGA also sends a drive signal to a first LED 415-1 and to a second LED 415-2. For example, a first drive signal at 80 kHz is transmitted across a first connection 416-1 to a first LED driver 412-1; and a second drive signal at 80 kHz is transmitted across a second connection 416-2 to a second LED driver 412-2. The second drive signal can be delayed in relation to the first drive signal. The drive signal can be a square wave.

The first LED driver 412-1 applies a signal to the first LED 415-1; the second LED driver 412-2 applies a signal to the second LED 415-2. The first LED 415-1 and the second LED 415-2 are part of the second optical source 312-2. The first LED 415-1 is configured to emit red light (e.g., wavelength W1); and the second LED 415-2 is configured to emit infrared light (e.g., wavelength W2).

The microcontroller 408 provides DC signals from digital-to-analog converters (DACs) to control intensity of light emitted by LEDs 415. DC signals from the DACs are combined with the drive signals to modulate output of light from the LEDs 415. In some embodiments, LEDs 415 are operated at full power, or near full power (e.g., equal to or greater than 75, 80, 90, 95, or 98% max power).

Figure 5:
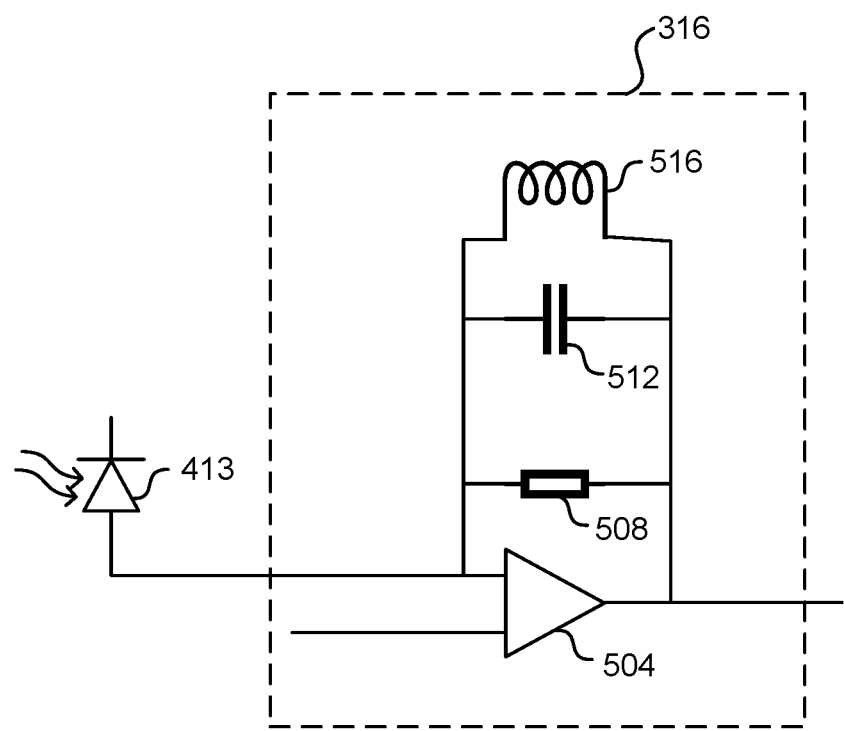
FIG. 5 is a diagram of an embodiment of an electrical network used in an herbicide sprayer system.

FIG. 5 is a diagram of an embodiment of an electrical network 316 used in an herbicide sprayer system. The electrical network 316 can include a transimpedence amplifier (TIA), a bandpass filter, and/or a zero-crossing detector. The electrical network 316 comprises an operational amplifier (op-amp) 504, a resistor 508, a capacitor 512, and an inductor 516. The op-amp 504, the resistor 508, and the capacitor 512 can be used for the TIA. The TIA is used to convert a current signal to a voltage signal.

The capacitor 512 and the inductor 516 are used for the bandpass filter. The capacitor 512 is a digital capacitor in that the capacitor 512 is digitally tuned (e.g., a digitally-tuned capacitor that is an integrated circuit variable capacitor). The capacitor 512 is electrically connected with the microcontroller 408 by the tuning connection 414. The microcontroller 408 changes voltage of the capacitor 512 so that the detect signal (generated by light from the first optical source 312-1 on the receive photodiode 413) is maximized.

Figure 6:
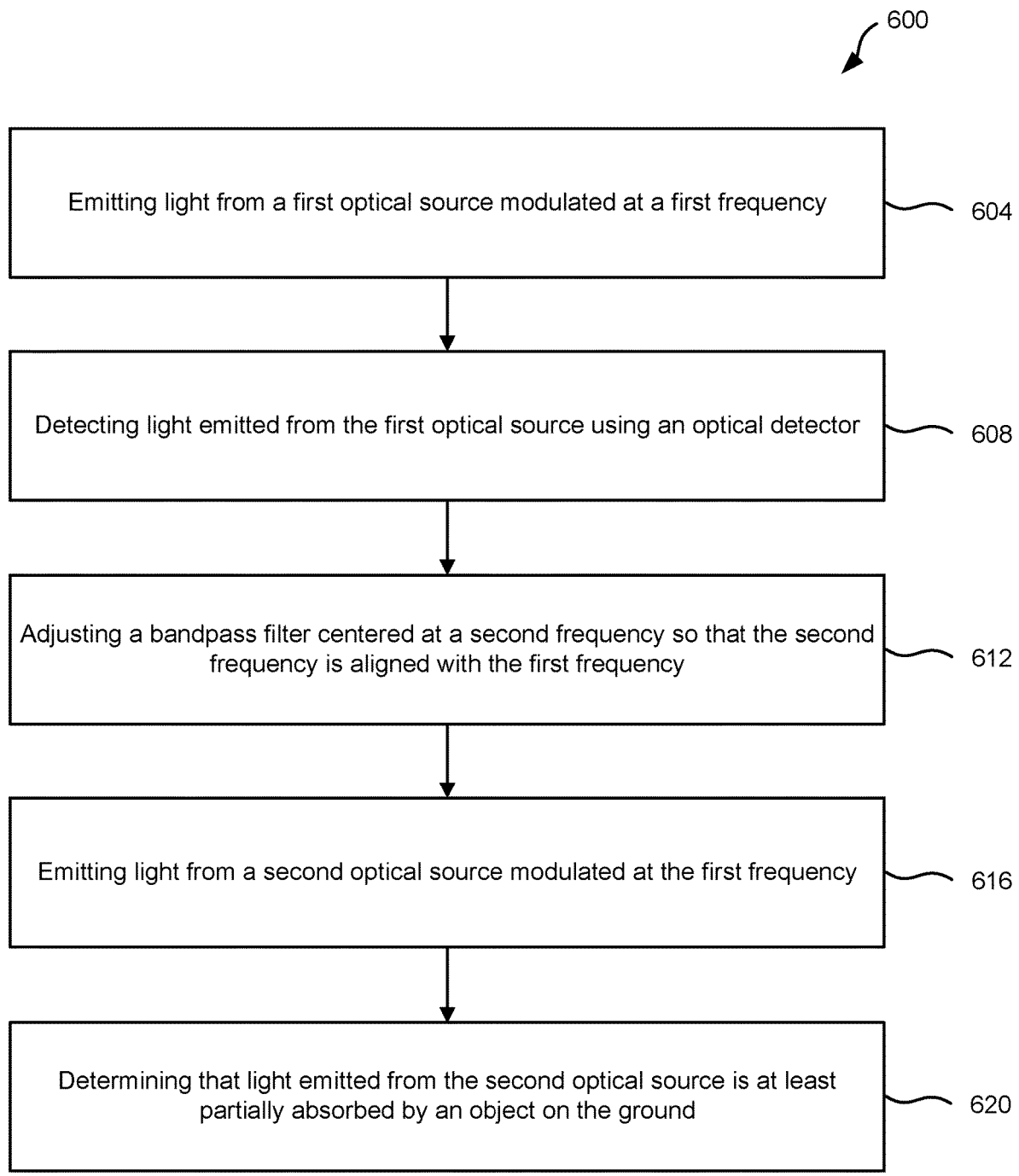
FIG. 6 is a flowchart of an embodiment of a process for calibrating and using an herbicide system.

FIG. 6 is a flowchart of an embodiment of a process 600 for calibrating and using an herbicide system. Process 600 begins in step 604 with emitting light from a first optical source (e.g., the first optical source 312-1) modulated at a first frequency (e.g., the first optical source 312-1 is modulated at 80 kHz). The first optical source 312-1 is oriented in the housing 304 so that light from the first optical source 312-1 does not have a straight optical path to exit the housing 304.

In step 608, light emitted from the first optical source 312-1 is detected using an optical detector (e.g., optical detector 308). A bandpass filter (e.g., comprising the capacitor 512 and the inductor 516 in FIG. 5), which is part of an electrical network (e.g., electrical network 316) coupled with the optical detector (e.g., receive photodiode 413), is adjusted using a controller (e.g., using microcontroller 408 of controller 320). The bandpass filter is centered at a second frequency. The bandpass filter is adjusted based on feedback from light detected by the optical detector from light emitted by the first optical source, so that the second frequency is aligned with the first frequency.

In step 616, light from a second optical source (e.g., the second optical source 312-2) is emitted. Light emitted from the second optical source is modulated at the first frequency (e.g., by an 80 kHz square-wave signal from the FPGA 404). The second optical source 312-2 is mounted in the housing, and there is a straight optical path from the second optical source 312-2 out of the housing 304 (e.g., optical path 324) and/or a straight optical path from the second optical source 312-2 to the ground (e.g., optical path 324).

In step 620, the controller 320 determines that light emitted from the second optical source 312-2 is at least partially reflected or absorbed by an object on the ground. Determining light is absorbed or reflected by an object on the ground is based on the detect signal from the optical detector 308 and the second frequency of the bandpass filter being aligned with the first frequency of the drive frequency. For example, the controller 320 determines that light is reflected from the weed 6 (a plant) and the herbicide system activates a solenoid valve 11 of a sprayer to spray a chemical (e.g., herbicide) on the object based on detecting that light from the second optical source 312-2 is at least partially absorbed and/or reflected. If the second frequency is not aligned with the first frequency, a signal generated by light from the second optical source 312-2 could be completely blocked by the bandpass filter, or partially blocked so that a signal-to-noise ratio drops below a threshold for detecting the object. In some embodiments the bandpass filter is calibrated during use (e.g., every 5, 10, 15, 20, 30, or 60 minutes; or calibration is tied to a GPS unit used to detect when a vehicle the system 300 is on (e.g., a tractor) is turning around or pauses for a given amount of time, such as 2, 3, 5, or 10 seconds); and/or the bandpass filter can be calibrated automatically at startup (or every second, third, fifth, or tenth startup). In some embodiments, a user selects a frequency of calibration (e.g., at startup and/or every 30 minutes during use). In some embodiments, the second optical source 312-2 can be turned off during calibration.

In some embodiments, the system 300 is configured to determine plant vigor in addition to, or in lieu of, spraying a chemical. For example, the system 300 could be configured to apply fertilizer, but applies fertilizer (or other application such as seed) to areas that do not have plants that have strong vigor (e.g., plants that are healthy are green; fertilizer, or seed, is then applied to areas that do not have green plants).

While the present invention has been described in terms of specific embodiments, it should be apparent to those skilled in the art that the scope of the present invention is not limited to the embodiments described herein. For example, features of one or more embodiments of the invention may be combined with one or more features of other embodiments without departing from the scope of the invention. The specification and drawings are, accordingly, to be regarded in an illustrative rather than a restrictive sense. Thus, the scope of the present invention should be determined not with reference to the above description, but should be determined with reference to the appended claims along with their full scope of equivalents.

What is claimed is:

1. A system for distributing herbicide, the system comprising:
   a housing;
   an optical detector in the housing;
   a first optical source, wherein:
      the first optical source is configured to be driven at a first frequency, and
      the first optical source is oriented in the housing so that light from the first optical source does not have a straight optical path to exit the housing;
   an electrical network electrically coupled with the optical detector, the electrical network comprising a bandpass filter configured to pass an electrical signal, wherein the bandpass filter is centered at a second frequency; and
   a controller configured to electronically adjust an electrical component of the bandpass filter to align the second frequency with the first frequency, such that the electrical network is calibrated for passing a modulated signal generated by the optical detector sensing light emitted from a second optical source modulated at the first frequency.

2. The system of claim 1, wherein:
   the system further comprises the second optical source, and
   the second optical source is oriented in the housing so that light from the second optical source has a straight optical path to exit the housing.

3. The system of claim 2, the second optical source comprising a first LED and a second LED, wherein the first LED and the second LED are oriented in the housing so that light from the first LED and the second LED have straight optical paths to exit the housing.

4. The system of claim 3, wherein the second LED has a different optical spectrum than the first optical source and a different optical spectrum than the first LED.

5. The system of claim 4, wherein the first optical source emits green light, the first LED emits red light, and the second LED emits light in the infrared.

6. The system of claim 2, wherein:
   the second optical source is configured to direct light to the ground; and
   the optical detector is configured to detect light reflected from the ground or an object on the ground.

7. The system of claim 6, wherein the controller is configured to activate a switch to spray herbicide in response to the optical detector detecting light reflected from a plant.

8. The system of claim 1, wherein the second frequency aligning with the first frequency is the second frequency equal to the first frequency, plus or minus 5%.

9. The system of claim 1, wherein light from the first optical source does not have an optical path to exit the housing.

10. The system of claim 1, wherein there is not a straight optical path from the first optical source to the optical detector.

11. The system of claim 10, wherein light from the first optical source is configured to reflect from the housing before reaching the optical detector.

12. The system of claim 1, wherein the first optical source is configured to run at less than half maximum power.

13. The system of claim 1, wherein the bandpass filter comprises a capacitor, and the capacitor is a digital capacitor.

14. The system of claim 1, wherein the electrical network further comprises a transimpedance amplifier and a zero-cross detector.

15. A method for calibrating and using an herbicide system, the method comprising:
   emitting light from a first optical source, wherein:
      the first optical source is modulated at a first frequency; and
      the first optical source is oriented in a housing so that light from the first optical source does not have a straight optical path to exit the housing;
   detecting light emitted from the first optical source using an optical detector;
   adjusting a bandpass filter, which is part of an electrical network electrically coupled with the optical detector, using a controller wherein:
      the bandpass filter is centered at a second frequency; and
      the bandpass filter is adjusted based on feedback from light detected by the optical detector from light emitted by the first optical source, so that the second frequency is aligned with the first frequency;
   emitting light from a second optical source, wherein:
      the second optical source is mounted in the housing, and
      the second optical source has a straight optical path from the second optical source to the ground; and
   determining that light emitted from the second optical source is at least partially absorbed by an object on the ground based on electrical signals from the optical detector and the second frequency being aligned with the first frequency.

16. The method of claim 15, wherein the second optical source is configured to emit light that stimulates fluorescence in a plant, and the optical detector is configured to detect emitted fluorescence light from the plant.

17. The method of claim 15, wherein the object on the ground is a plant and the method further comprises activating a sprayer to spray a chemical on the plant, based on the optical detector detecting that light from the second optical source is at least partially absorbed by the object.

18. A system for distributing herbicide, the system comprising:
   a housing;
   an optical detector in the housing;
   a first optical source, wherein:
      the first optical source is configured to be driven at a first frequency, and
      the first optical source is oriented in the housing to reflect light from the housing to be detected by the optical detector;
   an electrical network electrically coupled with the optical detector, the electrical network comprising a bandpass filter configured to pass an electrical signal, wherein the bandpass filter is centered at a second frequency; and
   a controller configured to electronically adjust an electrical component of the bandpass filter to align the second frequency with the first frequency, such that the electrical network is calibrated for passing a modulated signal generated by the optical detector sensing light emitted from a second optical source modulated at the first frequency.

19. The system of claim 18, wherein:
   the first optical source is configured in the housing to emit light to reflect off a panel of the housing to be detected by the optical detector after reflecting off the panel, and the panel is transparent or semitransparent.

20. The system of claim 19, wherein the panel in the housing is configured to not pass light from the first optical source toward the ground while the system is in use.

\* \* \* \* \*